United States Patent [19]

Suzuki et al.

[11] Patent Number: 4,569,837

[45] Date of Patent: Feb. 11, 1986

[54] PHARMACEUTICAL PREPARATION FOR REMEDY OF PERIODONTAL DISEASE AND PROCESS FOR PRODUCTION THEREOF

[75] Inventors: Yoshiki Suzuki; Hiroshi Ikura, both of Hino; Toshihide Noguchi, Tokyo; Katsunori Izumizawa, Yokohama; Shiro Kinoshita, deceased, late of Tokyo, all of Japan, by Kimiko Kinoshita, Atsuhiro Kinoshita, heirs

[73] Assignee: Teijin Limited, Osaka, Japan

[21] Appl. No.: 616,510

[22] Filed: Jun. 1, 1984

[30] Foreign Application Priority Data

Jun. 1, 1983 [JP] Japan ................. 58-95752

[51] Int. Cl.$^4$ ................. A61L 15/03; A61K 9/70; A61K 31; A61K 74
[52] U.S. Cl. ................. 424/28; 424/78; 514/953; 514/900; 514/902; 514/784
[58] Field of Search ................. 424/28, 78; 514/953, 514/900, 902, 781

[56] References Cited

U.S. PATENT DOCUMENTS 3,972,995  8/1976  Tsuk et al. ................. 424/28
4,292,299  9/1981  Suzuki et al. ................. 424/28

FOREIGN PATENT DOCUMENTS 822075     9/1969  Canada ................. 424/28
56-100714  8/1981  Japan ................. 424/28
WO80/00916 5/1980  PCT Int'l Appl. ................. 424/21
WO82/01129 4/1982  PCT Int'l Appl. ................. 424/28

*Primary Examiner*—Shep K. Rose
*Attorney, Agent, or Firm*—Sughrue, Mion, Zinn, Macpeak, and Seas

[57] ABSTRACT

A pharmaceutical preparation for remedy of periodontal diseases, which is in the form of a film or sheet and is inserted in a periodontal pocket or gingiva, said pharmaceutical preparation comprising a water-soluble polymeric substance having a Young's modulus of 10 to 250 Kg/mm$^2$ as determined at a temperature of 25° C. and a relative humidity of 65%, and a viscosity of the 2% aqueous solution of 5 to 30,000 CP as determined at 20° C. and a medicinal agent for remedy of periodontal diseases. This pharmaceutical preparation can be prepared by dissolving the above-mentioned water-soluble polymeric substance and medicinal agent in an organic solvent, casting the resultant solution, and removing the organic solvent by drying to obtain a pharmaceutical preparation in the form of a film or sheet.

9 Claims, No Drawings

PHARMACEUTICAL PREPARATION FOR REMEDY OF PERIODONTAL DISEASE AND PROCESS FOR PRODUCTION THEREOF

BACKGROUND OF THE INVENTION

1. Field of the Invention

The present invention relates to a pharmaceutical preparation for remedy of periodontal disease. More particularly, the present invention relates to a pharmaceutical preparation for remedy of periodontal diseases, which is in the form of a film or sheet and is inserted in a periodontal pocket or gingiva, comprising a medicinal agent for remedy of periodontal diseases, which has medicinal actions such as a germicidal action, an antibacterial action, a plaque-dissolving action and an anti-inflammatory action, and a water-soluble polymeric substance having a Young's modulus of 10 to 250 Kg/mm$^2$ as determined at a temperature of 25° C. and a relative humidity of 65%, and a viscosity of 5 to 30,000 CP as determined at 20° C. with respect to a 2% aqueous solution, and also relates to a process for the production of this pharmaceutical preparation for remedy of periodontal diseases.

2. Description of the Prior Art

By "periodontal diseases" are meant all diseases occurring in the periodontal tissue. The main periodontal diseases are gingivitis and chronic parodontitis marginalis. Chronic parodontitis marginalis is called "pyorrhea alveolaris", and 50 to 70% of adults of thirty years and over suffer from this diseases more or less. Pyorrhea alveolaris is a chronic disease of the periodontal tissue, the main complaints of which are the drainage of pus from the gingiva, the absorption of an alveolar bone, and the relaxation and tottering of teeth. It was considered that the main causes of pyorrhea alveolaris are general disorders such as hormone imbalance, abnormal metabolism, and avitaminosis but it has recently been proved that the main cause of pyorrhea alveolaris is a local inflammatory factor in the periodontal portion, which is due mainly to a plaque. The plaque is a bacterial plexus of oral bacteria, which is deposited on a groove of the tooth surface, a boundary between teeth, or a boundary between a tooth and gingiva. Inflammation is caused by bacteria in the plaque or metabolites thereof, and this inflammation extends to the deep portion to form a gingival pocket (periodontal pocket). This state is called pyorrhea alveolaris.

As the curative means, there are adopted an antiphlogistic treatment, a load relieving method, and a home curative treatment mainly for improving the affected gingival pocket and repairing the lesion of the periodontal tissue. According to the antiphlogistic treatment, the affected gingival pocket is improved by curettage of the affected gingival pocket, removal of tartar or cutting or cauterization of the gingiva, and the affected part is rendered antiphlogistic by washing and the injection of a medicine. According to the load relieving method, occlusion is adjusted, and according to the home curative treatment, teeth are cleaned and gingiva is massaged by the patient. Furthermore, there is adopted a method in which a solution of an antibacterial agent is irrigated or injected into the periodontal region and the interior of the periodontal pocket (see, for example, J. H. Hardy, H. N. Newman, J. D. Strahan; J. Clinical Periodontology, September 1982, pages 57-65). However, none of these methods have a decisive curative effect.

There has recently been reported a method in which an antibacterial agent is included in a strip composed of a water-insoluble polymeric substance such as poly(ethyl methacrylate) and the strip is placed in a periodontal pocket to kill anaerobic bacteria in the periodontal pocket [M. Addy et al.; J. Periodontol, November, 693 (1982)].

However, according to this method, since a water-insoluble polymeric substance is used, if the strip is left in the periodontal pocket, a pain or irritation is readily given to the affected part.

SUMMARY OF THE INVENTION

Accordingly, the object of the present invention is to provide a pharmaceutical preparation for remedy of periodontal diseases, which comprises a medicinal agent capable of killing bacteria and bacterial plexus in a periodontal pocket, which are fundamental causes of periodontal diseases, and of moderating inflammation, and a polymeric substance which has a flexibility such that the pharmaceutical preparation can be easily carried to the bottom of the periodontal pocket or the bottom of the gingival region as the boundary between the gingiva and teeth, such a water-solubility that, after the administration, the pharmaceutical preparation does not give an alien solid feeling causing a pain or irritation in the affected part and such physical properties that the polymetic substance is dissolved in the body fluid or extrudate to form a viscous liquid which is present in the periodontal pocket or gingival region for a certain time so that the medicinal agent is made resident in a part within the periodontal pocket or gingival region to increase the curative effect.

Another object of the present invention is to provide a process for the production of a pharmaceutical preparation for remedy of periodontal diseases.

Other objects and advantages of the present invention will be apparent from the following description.

In accordance with the present invention, there is provided a pharmaceutical preparation for remedy of periodontal diseases, which is in the form of a film or sheet and is inserted in a periodontal pocket or gingiva, comprising a water-soluble polymeric substance having a Young's modulus of 10 to 250 Kg/mm$^2$ as determined at a temperature of 25° C. and a relative humidity of 65%, and a viscosity of the 2% aqueous solution of 5 to 30,000 CP as determined at 20° C. and a medicinal agent for remedy of periodontal diseases.

In accordance with the present invention, there is also provided a process for the production the above-mentioned pharmaceutical preparation comprising the steps of dissolving a water-soluble polymeric substance having a Young's modulus of 10 to 250 Kg/mm$^2$ as determined at a temperature of 25° C. and a relative humidity of 65%, and a viscosity of the 2% aqueous solution of 5 to 30,000 CP as determined at 20° C. and a medicinal agent for remedying periodontal diseases.

DESCRIPTION OF THE PREFERRED EMBODIMENTS

Research was carried out with a view to developing a pharmaceutical preparation for remedy of periodontal diseases such as pyorrhea alveolaris, having a flexibility such as facilitating the arrival of the pharmaceutical preparation at the bottom of a periodontal pocket or gingival region, being capable of retaining a medicinal agent in the pocket for a long time, and giving no pain or irritation to the affected part. As the result, it was found that this object can be attained by the above-mentioned pharmaceutical preparation which is in the form of a film or sheet and is inserted in a periodontal pocket or gingiva.

According to the present invention, a water-soluble polymertic substance having a Young's modulus of 10 to 250 Kg/mm$^2$ as determined at a temperature of 25° C. and a relative humidity of 65%, and a viscosity of the 2% aqueous solution of 5 to 30,000 CP as determined at 20° C. is used as the base.

By the Young's modulus referred to in the present invention is meant the initial Young's modulus (Kg/mm$^2$) obtained when a sheet or film having a width of 1 cm and a thickness about 0.25 mm is pulled in a tensile strength tester at a chuck distance of 2 cm. When a water-soluble polymeric substance having such a flexibility that the Young's modulus is within the above-mentioned range is used, the obtained pharmaceutical preparation has a characteristic wherein the pharmaceutical preparation is administered, it can easily be guided to the bottom of a periodontal pocket or gingival region. By the term "periodontal pocket" used herein is meant a gingival pocket, that is, a groove or clearance formed between the tooth and gingiva by perodontitis or the like. Furthermore, by the term "gingival region" is meant a groove or clearance formed in the boundary between the tooth and gingiva by artificial means or a gingival portion left after curettage of a periodontal pocket. It is preferred that the Young's modulus of the polymeric substance be 15 to 200 Kg/mm$^2$, especially 20 to 180 Kg/mm$^2$.

It is indispensable in the present invention that the viscosity of a 2% aqueous solution of the water-soluble polymeric substance should be 5 to 30,000 CP as determined at 20° C. If a water-soluble polymeric substance having a viscosity included within the above-mentioned range is used, when the pharmaceutical preparation is inserted into a periodontal pocket or gingival region, the medicinal agent can be retained at an affected part of the periodontal pocket or gingival region for a long time without flowing-out of the medicinal agent and the curative effect of the medicinal agent can be exerted at a high efficiency. It is preferred that the viscosity of the polymeric substance be 10 to 27,000 CP especially 20 to 25,000 CP.

The base used in the present invention has the above-mentioned Young's modulus and viscosity and is a water-soluble polymeric substance having such a water solubility that is soluble in saliva or secreting fluid or exudate in the oral cavity. Since the pharmaceutical preparation of the present invention comprises this water-soluble polymeric substance, the surface portion of the preparation is dissolved by saliva or the like to some extent after administration into the periodontal pocket, and therefore, the preparation becomes adapted to the periodontal pocket or gingival region and the pain or irritation given to the affected part is moderated. This is one of advantage attained by the pharmaceutical preparation of the present invention.

It is preferred that the degree of the water solubility be such that when the water-soluble polymeric substance is compression-molded into a disc having a weight of about 500 mg, a diameter of 13 mm and a thickness of about 3 to about 4 mm and the solubility is tested in water according to the dissolution test method of the Japanese Pharmacopoeia (the stirring speed is 200 rpm and the liquid amount is 500 ml), more than 50% of the polymeric substance is not dissolved out within 30 minutes. When a water-soluble polymeric substance having a water solubility included within the above-mentioned range, the residence property of the pharmaceutical preparation inserted in a gingival region or periodontal pocket is improved.

As specific examples of the water-soluble polymeric substance, there can be mentioned lower alkyl ethers of cellulose such as methyl cellulose, hydroxyethyl cellulose, hydroxypropyl cellulose, hydroxypropylmethyl cellulose and sodium carboxymethyl cellulose, water-soluble vinyl polymers such as polyvinyl alcohol, polyvinyl pyrrolidone, polyacrylic acid, copolymers of methacrylic acid, styrene or a vinyl type ether monomer with acrylic acid and salts thereof, and alginic acid and the salts thereof, gelatin, pullulan, starch derivatives, and polyoxyalkylenes such as high molecular weight polyethylene glycol. Mixtures of two or more of these water-soluble polymeric substances also can be used. Among these water-soluble polymeric substances, lower alkyl ethers of cellulose, water-soluble vinyl polymers and mixtures of two or more of them are preferred, and methyl cellulose, sodium carboxymethyl cellulose, hydroxypropyl cellulose, hydroxypropylmethyl cellulose, polyvinyl pyrrolidone, a mixture of hydroxypropyl cellulose and polyacrylic acid or a salt thereof, and a mixture of hydroxypropyl cellulose and sodium carboxymethyl cellulose are especially preferred. Methyl cellulose, hydroxypropyl cellulose, and a mixture of hydroxypropyl cellulose and polyacrylic acid or its salt are most preferred.

Any of medicines effective for prevention and remedy of periodontal diseases can be used as the medicinal agent in the present invention. As the medicinal agent, there can be mentioned germicidal agents such as chlorohexidine, thimerosal, silver protein, chloramine, iodine glycerin, iodoform, boric acid, paraformaldehyde, phenol, hexylresorcinol, benzalkonium chloride, benzethonium chloride, chlorhexidine gluconate, phenododecium bromide, dequalinium chloride, cetylpyridinium chloride, and povidone iodine, antibacterial agents such as tetracycline, tetracycline hydrochloride, benzylpenicillin, ampicillin, carbenicillin, acetylkitasamycin, amoxyeillin, bacitracin, cephalotin sodium, cephaloridine, cephalexin, erythromycin, chloramphenicol, oxytetracycline hydrochloride, doxycycline hydrochloride, polymyxin B sulfate, fradiomycin sulfate, and gentamicin sulfate, plaque-dissolving agents such as lysozyme chloride, amylase, dextranase, and protease, anti-inflammatory agents such as sulpyrine, antipyrine, aspirin, phenylbutazone, meprizole, oxyphenbutazone, fenbufen, mefenamic acid, flurbiprofen, diclofenac sodium, ketoprofen, naproxen, tiaramid hydrochloride, benzydamine hydrochloride, alclofenac, ibufenac, perisoxalcitrate, ibuprofen, indomethacin, aluminum flufenamate, thinoridine hydrochloride, clofezone, dexamethasone, triamcinolone acetonide, and prostaglandin, antihistaminic agents such as diphenhydramine hydrochloride, chlorpheniramine maleate, and clemastine, antibiotic agents such as sulfathiazole, sulfisomidine, and acetylfuratrizine, and local anesthetic agents such as ethyl aminobenzoate and tetracaine hydrochloride. Mixtures of two or more of these medicinal agents may be used. Among these medicinal agents, germicidal agents, antibacterial agents, plaque-dissolving agents, and anti-inflammatory agents are preferred.

The amount used of the medicinal agent may be appropriately determined according to the intensity of the pharmacological activity of the medicinal agent used and the symptoms of the periodontal disease to be treated.

The pharmaceutical preparation of the invention of this application is inserted into the periodontal pocket or gingival region, and it is administered in the form of a film or sheet. The size, shape, and thickness of the pharmaceutical preparation can be changed according to the condition of the periodontal disease to be treated and they are not particularly critical. Ordinarily, the size, shape, and thickness of the pharmaceutical preparation are changed according to the size of the periodontal pocket of the patient or the condition of the gingiva. For example, a rectangular pharmaceutical preparation having a length of 5 to 15 mm, a width of 0.5 to 2.0 mm, and a thickness of 0.1 to 0.4 mm is used for a periodontal pocket, and a rectangular pharmaceutical preparation having a width of 10 to 30 mm, a length of 20 to 60 mm, and a thickness of 0.1 to 0.3 mm is used for a gingival portion left after curettage of a periodontal portion.

A plasticizer may be incorporated into the pharmaceutical preparation of the present invention according to need. As the plasticizer, there can be mentioned, for example, diethyl phthalate, dibutyl phthalate, butylphthalylbutyl glycolate, ethylene glycol, diethylene glycol, triethylene glycol, dipropylene glycol, polyethylene glycol, glycerin, and triacetin. When the plasticizer is incorporated, a pharmaceutical preparation in the form of a soft film or sheet suitable for administration into a periodontal pocket is obtained.

Furthermore, there may be used a colorant such as a tar pigment, a taste- or smell-improving agent such as citric acid, fumaric acid, tartaric acid or menthol, and an antioxidant such as butylhydroxytoluene, propyl gallate or butylhydroxyanisole, according to need.

The pharmaceutical preparation of the present invention can be produced by dissolving the above-mentioned water-soluble polymeric substance and the above-mentioned medicinal agent for remedy of periodontal diseases in a solvent, casting the obtained solution and removing the solvent by drying.

Any of these solvents capable of dissolving the respective components of the pharmaceutical preparation therein and inert to these components can be used in the present invention. For example, there can be mentioned alcohol type solvents such as methanol, ethanol, and isopropanol; ketone type solvents such as acetone and methylethyl ketone; chlorinated hydrocarbon type solvents such as methylene chloride, dichloroethane and 1,1,1-trichloroethane; and water. A mixture of two or more of these solvents can be used. An alcohol type solvent is preferred among these solvents.

It is preferred that the water-soluble polymeric substance be dissolved in the solvent in such an amount that the concentration is 3 to 50%, especially 5 to 40%, though the preferred concentration suitable for the production differs to some extent according to the molecular weight of the water-soluble polymeric substance. The medicinal agent is dissolved in an amount determined according to the intensity of the pharmacological activity of the medicinal agent. A plasticizer, a colorant, a taste- or smell-improving agent, and an antioxidant are dissolved in the solvent according to need. When the formed solution contains insoluble solids, they are removed by filtration, and it is preferred that the solution be allowed to stand still or be in vacuo for a while so that the solution is sufficiently deaerated. The solution is then cast. This casting is accomplished according to a method in which the solution is uniformly cast on a metal plate or glass plate, or by using a drum type film preparing apparatus customarily adopted in a solution casting method for production of films or an endless belt type film preparing apparatus.

Then, the solvent is removed by drying. Drying is accomplished by air-drying, standing at room temperature or heating, or according to the drying method customarily adopted in a film preparing apparatus. In view of the stability of the base and medicinal agent, it is preferred that drying the accomplished by air-drying or standing at room temperature. Thus, a pharmaceutical preparation in the form of a film or sheet is obtained. The film or sheet is cut into a desired shape. Thus, the intended pharmaceutical preparation is obtained.

Methods other than the above-mentioned method may be adopted for the production of a pharmaceutical preparation in the form of a film or sheet according to the present invention. For example, there may be adopted a calender method in which a mixture of a water-soluble polymeric substance and a medicinal agent is rolled between heated rolls to form a film or sheet, and a melt extrusion method in which a mixture of a water-soluble polymeric substance and a medicinal agent is heated and melted and the melt is extruded by a screw to form a film or sheet.

The obtained pharmaceutical preparation in the form of a film or sheet may be sterilized by heating or by ethylene oxide or radiation.

As described in detail hereinbefore, according to the present invention, a pharmaceutical preparation in the form of a film or sheet which comprises a water-soluble polymeric substance having specific Young's modulus and viscosity and a medicinal agent for remedy of periodontal diseases, and this pharmaceutical preparation has a flexibility such that it can be easily guided to the bottom of a periodontal pocket or gingival region and a property such that the medicinal agent can be retained within a local part of a periodontal pocket or gingival region and the pharmaceutical preparation moderates pains and irritations given to affected parts. Thus, excellent effects can be attained according to the present invention.

EXAMPLES

The present invention will now be described in detail with reference to, but is by no means limited to, the following Examples.

Example 1

100 g of hydroxypropyl cellulose having a viscosity of 2080 CP as determined at 20° C. (2% aqueous solution) and a Young's modulus of about 40 kg/mm$^2$ as determined at a temperature of 25° C. and relative humidity of 65% 1 g of chlorhexidine gluconate were gradually incorporated and dissolved with stirring in 1000 g of ethanol. The solution was allowed to stand still overnight to effect deaeration, the solution was cast on a clean glass plate, and the thickness was uniformalized by using a doctor knife. The cast solution was air-dried and forcibly dried at 40° C. to obtain a pharmaceutical preparation in the form of a film having a thickness of 0.26 mm. The concentration of chlorhexidine gluconate in the pharmaceutical preparation was 0.98%. The Young's modulus of the film was about 40

Kg/mm$^2$ as determined at a temperature of 25° C. and a relative humidity of 65%.

Example 2

100 g of hydroxypropyl cellulose having a viscosity of 2080 CP as determined at 20° C. (2% aqueous solution) and a Young's modulus of 48.2 Kg/mm$^2$ as determined at a temperature of 25° C. and a relative humidity of 65% and 1.0 g of chlorhexidine were gradually incorporated and dissolved with stirring into 1000 g of ethanol. The solution was allowed to stand still overnight to effect deaeration and cast on a clean glass plate. The thickness was uniformalized by using a doctor knife, and the cast solution was air-dried and forcibly dried at 40° C. to obtain a pharmaceutical preparation in the form of a film having a thickness of 0.26 mm. The concentration of chlorhexidine in the obtained pharmaceutical preparation was 0.98%.

Example 3

80 g of hydroxypropyl cellulose having a viscosity of 2080 CP as determined at 20° C. (2% aqueous solution) and a Young's modulus of 48.2 Kg/mm$^2$ as determined at a temperature of 25° C. and a relative humidity of 65% and 20 g of tetracycline hydrochloride were gradually incorporated and dissolved with stirring in 960 g of ethanol. The solution was allowed to stand still overnight to effect deaeration, and the solution was cast on a clean glass plate and the thickness was uniformalized by using a doctor knife. The cast solution was air-dried and forcibly dried at 40° C. to obtain a pharmaceutical preparation in the form of a film having a thickness of 0.25 mm. The concentration of tetracycline hydrochloride in the pharmaceutical preparation was 19.8%.

Example 4

100 g of hydroxypropyl cellulose having a viscosity of 200 CP as determined at 20° C. (2% aqueous solution) and a Young's modulus of 39.1 Kg/mm$^2$ as determined at a temperature of 25° C. and a relative humidity of 65% and 1 g of cetyl pyridinium chloride were gradually incorporated and dissolved with stirring in 960 g of ethanol. The solution was allowed to stand still overnight to effect deaeration and cast on a clean glass sheet. The thickness was uniformalized by using a doctor knife and the cast solution was air-dried and forcibly dried at 40° C. to obtain a pharmaceutical preparation in the form of a film having a thickness of 0.27 mm. The concentration cetyl pyridinium chloride in the pharmaceutical preparation was 1.0%.

Example 5

75 g of hydroxypropyl cellulose having a viscosity of 200 CP as determined at 20° C. (2% aqueous solution) and a Young's modulus of 39.1 Kg/mm$^2$ as determined at a temperature of 25° C. and a relative humidity of 65%, 25 g of sodium polyacrylate and 10 g of amoxycillin were gradually incorporated and dissolved with stirring in 960 g of an aqueous solution of ethanol. The solution was allowed to stand still overnight to effect deaeration and cast on a clean glass plate, the thickness was uniformalized by using a doctor knife, and the cast solution was air-dried and forcibly dried at 40° C. to obtain a pharmaceutical preparation in the form of a film having a thickness of 0.28 mm. The concentration of amoxycillin in the pharmaceutical preparation was 8.5%.

Example 6

90 g of methyl cellulose having a viscosity of 4160 CP as determined at 20° C. (2% aqueous solution) and a Young's modulus of 125 Kg/mm$^2$ as determined at a temperature of 25° C. and a relative humidity of 65% and 10 g of fradiomycin sulfate were incorporated and dissolved with stirring in 1000 g of ethanol, and the solution was allowed to stand still overnight to effect deaeration. The solution was cast on a clean glass plate, the thickness was uniformalized by using a doctor knife, and the cast solution was air-dried and forcibly dried at 40° C. to obtain a pharmaceutical preparation in the form of a film having a thickness of 0.20 mm. The concentration of fradiomycin sulfate in the pharmaceutical preparation was 9.8%.

Example 7

95 g of methyl cellulose having a viscosity of 4160 CP as determined at 20° C. (2% aqueous solution) and a Young's modulus of 125 Kg/mm$^2$ as determined at a temperature of 25° C. and a relative humidity of 65% and 5 g of ketoprofen were gradually incorporated and dissolved with stirring in 1000 g of ethanol. The solution was allowed to stand still overnight to effect deaeration and cast on a clean glass plate. The thickness was uniformalized by using a doctor knife and the cast solution was air-dried and forcibly dried at 40° C. to obtain a pharmaceutical preparation in the form of a film having a thickness of 0.29 mm. The concentration of ketoprofen in the pharmaceutical preparation was 4.8%.

Example 8

95 g of methyl cellulose having a viscosity of 9670 CP as determined at 20° C. (2% aqueous solution) and a Young's modulus of 130 Kg/mm$^2$ as determined at a temperature of 25° C. and a relative humidity of 65% and 5 g of indomethacin were gradually incorporated and dissolved with stirring in 960 g of ethanol. The solution was allowed to stand still overnight to effect deaeration, the solution was cast on a clean glass plate, and the thickness was uniformalized by using a doctor knife. The cast solution was air-dried and forcibly dried at 40° C. to obtain a pharmaceutical preparation in the form of a film having a thickness of 0.25 mm. The concentration of indomethacin in the pharmaceutical preparation was 5.0%.

Example 9

90 g of methyl cellulose having a viscosity of 15 CP as determined at 20° C. (2% aqueous solution) and a Young's modulus of 151 Kg/mm$^2$ as determined at a temperature of 25° C. and a relative humidity of 65%, 10 g of sodium carboxymethyl cellulose and 1 part by weight of clemastine fumarate were gradually incorporated and dissolved with stirring in 960 g of 90% aqueous ethanol. The solution was allowed to stand still overnight to effect deaeration, the solution was cast on a clean glass plate, and the thickness was uniformalized by using a doctor knife. The cast solution was air-dried and forcibly dried at 40° C. to obtain a pharmaceutical preparation in the form of a film having a thickness of 0.30 mm. The concentration of clemastine fumarate in the pharmaceutical preparation was 1.0%.

Example 10

100 g of hydroxyethyl cellulose having a viscosity of 5140 CP as determined at 20° C. (2% aqueous solution)

and a Young's modulus of 50 Kg/mm$^2$ as determined at a temperature of 25° C. and a relative humidity of 65% and 1 g of ethyl aminobenzoate were gradually incorporated and dissolved with stirring in 960 g of ethanol. The solution was allowed to stand still overnight to effect deaeration, cast on a clean glass plate, and the thickness was uniformlaized by using a doctor knife. The cast solution was air-dried and forcibly dried at 40° C. to obtain a pharmaceutical preparation in the form of a film having a thickness of 0.30 mm. The concentration of ethyl aminobenzoate in the pharmaceutical preparation was 0.95%.

Example 11

100 g of hydroxyethyl cellulose having a viscosity of 5140 CP as determined at 20° C. (2% aqueous solution) and a Young's modulus of 50 kg/mm$^2$ as determined at a temperature of 25° C. and a relative humidity of 65% and 1 g of dequalinium chloride were gradually incorporated and dissolved with stirring in 960 g of ethanol. The solution was allowed to stand still overnight to effect deaeration, cast on a clean glass plate, and the thickness was uniformalized by using a doctor knife and the cast solution was air-dried and forcibly dried at 40° C. to obtain a pharmaceutical preparation in the form of a film having a thickness of 0.26 mm. The concentration of dequalinium chloride in the pharmaceutical preparation was 0.95%.

Example 12

100 g of hydroxypropyl cellulose having a viscosity of 2080 CP as determined at 20° C. (2% aqueous solution) and a Young's modulus of 48.2 kg/mm$^2$ as determined at a temperature of 25° C. and a relative humidity of 65% and 1.0 g of chlorhexidine gluconate were gradually incorporated and dissolved with stirring into 1000 g of water. The solution was deaerated in vacuo for 2 hrs and cast on a clean glass plate. The thickness was uniformalized by using a doctor knife, and the cast solution was air-dried and forcibly dried at 40° C. to obtain a pharmaceutical preparation on the form of a film having a thickness of 0.25 mm. The concentration of chlorhexidine in the obtained pharmaceutical preparation was 0.98%.

Example 13

Filmy pharmaceutical preparations prepared in Examples 1 and 2 were cut into a width of 1 mm and a length of 10 mm, and cut pieces were inserted in periodontal pockets of 10 patients suffering from pyorrhea alveolaris and the pain, drainage of pus, swelling, flare, fever, and loose feeling were checked before and after the administration. Effects were observed in all the patients, and the pain was prominently reduced and the fever was controlled. These effects were retained for 2 to 3 days by one administration. Thus, the effectiveness of the pharmaceutical preparation of the present invention was proved.

Example 14

A pharmaceutical preparation in the form of a film was prepared in the same manner as described in Example 1 by using hydroxypropyl cellulose having a viscosity of 4000 CP and a Young's modulus of 50 Kg/mm$^2$ as determined at a temperature of 25° C., and a relative humidity of 65%, which was dissolved out in an amount smaller than 10% for 30 minutes when the dissolution speed of a disc of the hydroxypropyl cellulose having a weight of 500 mg, a diameter of 13 mm, and a thickness of 3 mm, which was obtained by compression molding, was measured in water at 37° C. according to the method of the Japanese Pharmacopoeia (the stirring speed was 200 rpm and the liquid amount was 500 ml).

When this filmy pharmaceutical preparation was administered into a periodontal pocket of a patient suffering from pyorrhea alverolaris, the pharmaceutical preparation was retained for a long time and the pain was prominently reduced.

Comparative Example 1

A filmy pharmaceutical preparation was prepared in the same manner as described in Example 1 by using hydroxypropyl cellulose having a viscosity of 3 CP as determined at 20° C. (2% aqueous solution). When this preparation was administered into a periodontal pocket of a patient suffering from pyorrhea alverolaris, at the moment the top end of the preparation was inserted into the periodontal pocket, the top end portion and the portion falling in contact with an exudate became softened, and insertion of the subsequent portion became difficult. Even if the preparation could be inserted, the medicinal agent retaining property was extremely poor.

In case of a filmy pharmaceutical preparation composed of sodium polyacrylate having a Young's modulus lower than 10 Kg/mm$^2$, insertion into a periodontal pocket was difficult because the preparation was too soft. In case of a filmy pharmaceutical preparation composed of polyvinyl alcohol having a Young's modulus of 297 Kg/mm$^2$, a periodontal pocket was readily hurt and the pain was violent at the time of insertion because the preparation was too hard.

Comparative Example 2

Polymethyl methacrylate, a kind of a water-insoluble polymeric substance, was used as the base and dissolved in dichloromethane, and chlorhexidine gluconate was suspended in the solution. A filmy pharmaceutical preparation was produced in the same manner as described in Example 1 by using the so-obtained suspension.

When this filmy pharmaceutical preparation was administered into a periodontal pocket of a patient suffering from pyorrhea alverolaris, the pain was not moderated, and the preparation was not suitable as a drug.

Example 15

95 g of hydroxypropyl cellulose having a viscosity of 2080 CP as determined at 20° C. (2% aqueous solution) and a Young's modulus of 48.2 Kg/mm$^2$ as determined at a temperature of 25° C. and a relative humidity of 65% and 5 g of chlorhexidine gluconate were gradually dissolved with stirring in 1000 g of ethanol. The solution was allowed to stand still overnight to effect deaeration, the solution was cast on a clear glass plate, and the thickness was uniformalized by using a doctor knife. The cast solution was air-dried and forcibly dried at 40° C. to obtain a pharmaceutical preparation in the form of a film. The film was cut into a width of 1 mm and a length of 10 mm. Thus, the pharmaceutical preparation in the form of a strip having a thickness of 0.3 mm and a size of 1 mm×10 mm was obtained. As a control, the same strips containing no chlorohexidine gluconate were prepared in the same manner as mentioned above.

These strips were inserted in periodontal pockets of 5 patients with advanced periodontal diseases and having at least a pair of deep pockets contralaterally in such a manner that the strips containing chlorohexidine gluconate (i.e., the present samples) were inserted into one pocket and the control samples were inserted into the other pocket. Thus, the microbiological and clinical effects of the samples were evaluated as follows:

(a) Plaque Index: see Silness, J. and Löe, H.: Periodontal disease in pregnancy, II. Correlation between oral hygiene and periodontal condition. Acta Odont. Scand., 22: 121–135, 1964

(b) Gingival Index: see Löe, H., and Silness, J.: Periodontal disease in pregnancy, I. Prevalence and severity. Acta Odont. Scand., 21: 121–135, 1964

(c) Pocket Depth: The depth at which the strips are reached.

(d) Breeding: The presence (+) of breeding is determined when the strips are inserted into the pockets or when the subgingival plaque is sampled.

The test results were obtained on 0, 2, 4, and 6 days. The results are shown in Tables 1 and 2.

TABLE 1

| | | | | (Control side) | | | | | | | | | | | | | | |
|---|---|---|---|---|---|---|---|---|---|---|---|---|---|---|---|---|---|---|
| | | | | Plaque index (day) | | | | Gingival index | | | | Pocket depth (mm) | | | | Bleeding | | | |
| Patient | Age | Sex | Portion | 0 | 2 | 4 | 6 | 0 | 2 | 4 | 6 | 0 | 2 | 4 | 6 | 0 | 2 | 4 | 6 |
| A | 32 | f | ⎡4 | 1 | 1 | 1 | 1 | 2 | 2 | 2 | 2 | 6 | 6 | 6 | 6 | + | + | + | + |
| B | 43 | m | ⎡6 | 3 | 2 | 1 | 2 | 2 | 2 | 2 | 2 | 10 | 10 | 10 | 10 | + | + | + | + |
| C | 62 | m | ⎿2 | 2 | 2 | 2 | 2 | 2 | 2 | 2 | 2 | 5 | 5 | 5 | 5 | + | – | + | – |
| D | 43 | m | ⎿6 | 2 | 2 | 2 | 2 | 2 | 2 | 2 | 2 | 6 | 6 | 6 | 6 | + | + | + | + |
| E | 58 | m | ⎿2 | 1 | 1 | 1 | 1 | 2 | 2 | 2 | 2 | 7 | 7 | 7 | 7 | + | + | – | + |

TABLE 2

| | | | | (Experimental side) | | | | | | | | | | | | | | |
|---|---|---|---|---|---|---|---|---|---|---|---|---|---|---|---|---|---|---|
| | | | | Plaque index (day) | | | | Gingival index | | | | Pocket depth (mm) | | | | Bleeding | | | |
| Patient | Age | Sex | Portion | 0 | 2 | 4 | 6 | 0 | 2 | 4 | 6 | 0 | 2 | 4 | 6 | 0 | 2 | 4 | 6 |
| A | 32 | f | 4⏋ | 1 | 1 | 1 | 1 | 3 | 3 | 2 | 2 | 6 | 6 | 6 | 5 | + | + | – | – |
| B | 43 | m | 6⏋ | 3 | 1 | 1 | 1 | 2 | 1 | 1 | 1 | 8 | 8 | 8 | 7 | + | – | – | – |
| C | 62 | m | ⎿2 | 2 | 2 | 1 | 1 | 2 | 2 | 1 | 1 | 5 | 5 | 4 | 4 | + | – | – | – |
| D | 43 | m | 6⏌ | 2 | 1 | 1 | 1 | 2 | 1 | 1 | 1 | 7 | 6 | 5 | 5 | + | – | – | – |
| E | 58 | m | 2⏌ | 1 | 1 | 1 | 1 | 2 | 2 | 2 | 2 | 8 | 7 | 7 | 7 | + | – | – | – |

$Kg/mm^2$ as determined at a temperature of 25° C. and a relative humidity of 65%.

3. The method of remedying periodontal diseases as claimed in claim 1, wherein the viscosity of a 2% aqueous solution of the water-soluble polymeric substance is 10 to 27,000 CP as determined at 20° C.

4. The method of remedying periodontal diseases as claimed in claim 1, wherein the water-soluble polymeric substance is a polysaccharide, a derivative thereof, a water-soluble vinyl polymer or a mixture thereof.

5. The method of remedying periodontal diseases as claimed in claim 4, wherein the polysaccharide or derivative thereof is a lower alkyl ether of cellulose.

6. The method of remedying periodontal diseases as claimed in claim 5, wherein the lower alkyl ether of cellulose is methyl cellulose, hydroxyethyl cellulose, hydroxypropyl cellulose, sodium carboxymethyl cellulose or a mixture of two or more of said cellulose derivatives.

7. The method of remedying periodontal diseases as claimed in claim 4, wherein the water-soluble vinyl polymer is polyvinyl alcohol or polyvinyl pyrrolidone.

8. The method of remedying periodontal diseases as claimed in claim 1, wherein the water-soluble polymeric substance is a mixute of methyl cellulose, hydroxypropyl cellulose or hydroxypropyl cellulose with polyacrylic acid or a salt thereof.

9. The method of remedying periodontal diseases as claimed in claim 1, wherein the medicinal agent for remedy of periodontal diseases has germicidal action, an antibacterial action, a plaque-dissolving action or an anti-inflammatory action.

* * * * *

What is claimed is:

1. A method of remedying periodontal diseases comprising inserting a pharmaceutical preparation in the form of a film or sheet into a periodontal pocket or gingival region, wherein said pharmaceutical preparation consists essentially of a water-soluble polymeric substance having a Young's modulus of 10 to 250 $Kg/mm^2$ as determined at a temperature of 25° C. and a relative humidity of 65%, and a viscosity of a 2% aqueous solution of 5 to 30,000 CP as determined at 20° C. and a medicinal agent for periodontal disease.

2. The method of remedying periodontal diseases as claimed in claim 1, wherein the Young's modulus of the water-soluble polymeric substance is 15 to 200